US011103312B2

(12) United States Patent
Venkataraman

(10) Patent No.: US 11,103,312 B2
(45) Date of Patent: Aug. 31, 2021

(54) METHOD AND SYSTEM FOR PREDICTING CURRENT PATHS AND EVALUATING ELECTRICAL BURN RISKS OF A MONOPOLAR ELECTROSURGERY TOOL

(71) Applicant: Verb Surgical Inc., Mountain View, CA (US)

(72) Inventor: Jagadish Venkataraman, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 265 days.

(21) Appl. No.: 16/372,852

(22) Filed: Apr. 2, 2019

(65) Prior Publication Data
US 2020/0315707 A1    Oct. 8, 2020

(51) Int. Cl.
*A61B 34/10*    (2016.01)
*A61B 18/16*    (2006.01)
(Continued)

(52) U.S. Cl.
CPC ............. *A61B 34/10* (2016.02); *A61B 18/16* (2013.01); *A61B 90/361* (2016.02); *A61B 90/37* (2016.02);
(Continued)

(58) Field of Classification Search
CPC ... A61B 34/10; A61B 18/16; A61B 2034/101; A61B 2018/1253; A61B 2018/00684;
(Continued)

(56) References Cited

U.S. PATENT DOCUMENTS 5,766,165 A    6/1998 Gentelia et al.
2010/0087810 A1    4/2010 Odell et al.
(Continued)

FOREIGN PATENT DOCUMENTS

EP    2223666    9/2010
WO    2005046497    5/2005

OTHER PUBLICATIONS

Bifulco, Paolo, et al., "Investigating the role of capacitive coupling between the operating table and the return electrode of an electrosurgery unit in the modification of the current density distribution within the patients' body", BioMedical Engineering OnLine, vol. 12, No. 80, 2013, 12 pages.
(Continued)

*Primary Examiner* — Joseph A Stoklosa
*Assistant Examiner* — Christopher Patrick Gloth
(74) *Attorney, Agent, or Firm* — Womble Bond Dickinson (US) LLP

(57) ABSTRACT

Embodiments described herein provide various examples of predicting potential current paths from an active electrode of a monopolar electrosurgery tool to a return electrode of the monopolar electrosurgery tool based on analyzing electrical properties of tissues inside a patient's body, and evaluating and eliminating tissue burn risks associated with the predicted current paths. In some embodiments, a current-path-prediction technique is used to predict a set of potential current paths from the active electrode to the return electrode for any given geometrical configuration of the two electrodes on the patient's body. These predicted current paths can then be pictorially displayed on a 3D scan of the patient's body or an endoscopic view of the patient's body and in relation to the display of any existing metal implant inside the patient's body, which allows for visualizing points of tissue burn risks inside the patient's body.

20 Claims, 4 Drawing Sheets

(51) Int. Cl.
*A61B 90/00* (2016.01)
*A61B 18/12* (2006.01)
*A61B 18/00* (2006.01)

(52) U.S. Cl.
CPC .............. *A61B 2018/00684* (2013.01); *A61B 2018/1253* (2013.01); *A61B 2018/167* (2013.01); *A61B 2034/101* (2016.02)

(58) Field of Classification Search
CPC .............. A61B 90/37; A61B 2034/107; A61B 18/1233
See application file for complete search history.

(56) References Cited

U.S. PATENT DOCUMENTS

| | | | | |
|---|---|---|---|---|
| 2019/0340793 | A1* | 11/2019 | Jin | G06T 11/005 |
| 2020/0085504 | A1* | 3/2020 | Schwartz | A61B 5/066 |
| 2020/0297415 | A1* | 9/2020 | Marshik | A61B 90/361 |
| 2021/0007805 | A1* | 1/2021 | Liu | A61B 34/10 |
| 2021/0100613 | A1* | 4/2021 | Baril | A61B 18/1206 |

OTHER PUBLICATIONS

International Search Report and Written Opinion for International Application No. PCT/US2019/060635 dated Apr. 9, 2020, 10 pages.

\* cited by examiner

METHOD AND SYSTEM FOR PREDICTING CURRENT PATHS AND EVALUATING ELECTRICAL BURN RISKS OF A MONOPOLAR ELECTROSURGERY TOOL

TECHNICAL FIELD

The present disclosure generally relates to monopolar electrosurgery and, more specifically, to systems, devices and techniques for predicting potential current paths from an active electrode of a monopolar electrosurgery tool to a return electrode of the monopolar electrosurgery tool, and evaluating and eliminating tissue burn risks associated with the predicted current paths.

BACKGROUND

Generally speaking, there are two main types of electrosurgery tools: bipolar electrosurgery tools and monopolar electrosurgery tools. A bipolar electrosurgery tool typically includes a pair of forceps-like electrodes: the electrical current flows from one tip of the forceps-like tool (i.e., the first electrode) to the other tip of the forceps-like tool (i.e., the second electrode) through the target tissue between the two tips, so that the current does not actually go into a patient's body. In contrast, in a monopolar electrosurgery tool, an active electrode of the monopolar electrosurgery tool is placed at the surgical site of a patient. A return electrode of the monopolar electrosurgery tool (also known as the "dispersive pad" or the "grounding pad") is placed somewhere else on the patient's body, which is often on the opposite side of the patient's body to where the surgical site and the active electrode are located. Hence, the main electrical current of the monopolar electrosurgery tool flows from the active electrode to the return electrode/grounding pad through the patient's body following a path of least resistance as it completes a full circuit.

While bipolar electrosurgery tools are still being used in some electrosurgery procedures, it can be quite difficult to find enough space to place both electrodes around a small surgical site. In contrast, a monopolar electrosurgery tool, which only uses the active electrode at the surgical site, can be much easier to place and convenient to work with. However, because the patient's body is used as a part of the current return path in monopolar electrosurgery, cares must be taken to prevent accidental tissue burns inside the patient's body, especially when there are metal objects, such as metal implants inside the patient's body.

SUMMARY

This patent disclosure provides various embodiments of predicting potential current paths from an active electrode of a monopolar electrosurgery tool to a return electrode/grounding pad of the monopolar electrosurgery tool based on analyzing electrical properties of tissues inside a patient's body, and evaluating and eliminating tissue burn risks associated with the predicted current paths. In some embodiments, a disclosed current-path-prediction technique is designed to predict a set of potential current paths from the active electrode to the grounding pad for any given geometrical configuration of the two electrodes on the patient's body. These predicted current paths can then be pictorially displayed on a three-dimensional (3D) scan of the patient's body or an endoscopic view of the patient's body and in relation to the display of any existing metal implant inside the patient's body, thereby allowing for visualizing points of tissue burn risks inside the patient's body. For example, when a predicted current path intersects the location of a metal implant inside the patient's body, a potential tissue burn risk is identified and the location where the current path meets the metal implant can be highlighted.

Based on the display of the predicted current paths and highlighted locations of tissue burn risks, surgical staff can choose to reposition the grounding pad of the monopolar electrosurgery tool to alter the potential current paths. The disclosed current-path-prediction technique can then be applied to the new electrodes configuration to generate another set of potential current paths from the active electrode to the new grounding pad location. Next, the potential tissue burn risks can be reevaluated for the new set of potential current paths inside the patient's body. If one or more tissue burn risks are identified for the new set of potential current paths, the grounding pad can be reposition again, and this current prediction-evaluation procedure can be repeated. Moreover, the predicted current paths can also reveal any accidental contact of a part of the patient body with a grounded metal object, such as the surgery table or a metal tray table. Such a body/metal contact can cause a current to bypass the grounding pad and flow to the body/metal contact location, causing accidental tissue burns. Hence, based on the evaluation outputs and display of the predicted current paths which highlights the locations of such burn risks, surgical staff can reposition the patient's body to prevent accidental contacts between the patient's body and the grounded metal objects.

In one aspect, a process for predicting potential current paths within a patient's body when using a monopolar electrosurgery tool on the patient is disclosed. This process can begin by receiving locations of an active electrode and a return electrode of the monopolar electrosurgery tool on the patient's body. The process next identifies a set of tissues between the locations of the active electrode and the return electrode. The process subsequently augments each of the set of identified tissues with a corresponding value of an electrical property, such as a dielectric constant value. Next, the process uses a current path model, the set of identified tissues, and the set of corresponding values of the electrical property to predict a set of potential current paths between the active electrode and the return electrode.

In some embodiments, the process identifies the set of tissues between the locations of the active electrode and the return electrode by: receiving a three-dimensional (3D) scan of the patient's body; segmenting anatomical structures between the locations of the active electrode and the return electrode based on the received 3D scan; and identifying the set of tissues from the segmented anatomical structures.

In some embodiments, the process identifies the set of tissues between the locations of the active electrode and the return electrode by: receiving an endoscope video which captures anatomical structures inside the patient's body along the way between the active electrode and the return electrode; and segmenting the captured anatomical structures to identify the set of tissues.

In some embodiments, the process further identifies a set of dimensions for each of the set of identified tissues based on the segmented anatomical structures.

In some embodiments, the process further includes the steps of: extracting from the 3D scan, locations and dimensions of one or more metal implants inside the patient's body; and providing the extracted locations and dimensions of the one or more metal implants to the current path model as inputs for predicting the set of potential current paths.

In some embodiments, the process augments each of the set of identified tissues with a corresponding dielectric constant value using a look-up table containing estimated dielectric constants of various types of tissues within a human body.

In some embodiments, augmenting each of the set of identified tissues with a corresponding dielectric constant further includes the steps of: extracting color information for an identified tissue in the set of identified tissues from endoscope video images of anatomical structures inside the patient's body along the way between the active electrode and the return electrode; converting the color information into a modifier to modify a corresponding dielectric constant value associated with the identified tissues from the look-up table; and augmenting the identified tissue with the modified dielectric constant value.

In some embodiments, the process further computes a probability value for each of the set of potential current paths, wherein a potential current path in the set of potential current paths having a lower overall resistance is associated with a higher probability value.

In some embodiments, the process further includes the steps of: displaying one or more potential current paths in the set of potential current paths which has the highest probability values; and for each of the displayed potential current paths, highlighting one or more locations of potential tissue burn injuries due to the potential current path flows through a metal implant and/or the potential current path flows through a part of the patient's body touching a grounded metal object.

In another aspect, a system for predicting potential current paths within a patient's body when using a monopolar electrosurgery tool on the patient is disclosed. This system can include: one or more processors and a memory coupled to the one or more processors. Moreover, the one or more processors are configured to: receive locations of an active electrode and a return electrode of the monopolar electrosurgery tool on the patient's body; identify a set of tissues between the locations of the active electrode and the return electrode; augment each of the set of identified tissues with a corresponding value of an electrical property; and predict a set of potential current paths between the active electrode and the return electrode and potential tissue burn associated with each of the set of potential current paths based on a current path model, the set of identified tissues, and the set of corresponding values of the electrical property.

In some embodiments, the system identifies the set of tissues between the locations of the active electrode and the return electrode by: receiving a three-dimensional (3D) scan of the patient's body; segmenting anatomical structures between the locations of the active electrode and the return electrode based on the received 3D scan; and identifying the set of tissues from the segmented anatomical structures.

In some embodiments, the system identifies the set of tissues between the locations of the active electrode and the return electrode by: receiving an endoscope video which captures anatomical structures inside the patient's body along the way between the active electrode and the return electrode; and segmenting the captured anatomical structures to identify the set of tissues.

In some embodiments, the one or more processors are further configured to: extract from the 3D scan, locations and dimensions of one or more metal implants inside the patient's body; and provide the extracted locations and dimensions of the one or more metal implants to the current path model as inputs for predicting the set of potential current paths.

In some embodiments, the system further includes a display device, and the one or more processors are further configured to: display on the display device one or more potential current paths in the set of potential current paths which has the highest probability values; and for each of the displayed potential current paths, highlight one or more locations of potential tissue burn injuries due to the potential current path flows through a metal implant and/or the potential current path flows through a part of the patient's body touching a grounded metal object.

In yet another aspect, a process for using a current-path-prediction procedure to eliminate risks of accidental tissue burns when using a monopolar electrosurgery tool on a patient is disclosed. This process can begin by receiving initial locations of an active electrode and a return electrode of the monopolar electrosurgery tool on the patient's body. Next, the process uses a current-path-prediction model to generate a first set of predicted current paths inside the patient's body between the initial locations of the active electrode and the return electrode. The process next determines if any of the first set of predicted current paths can cause potential tissue burn injuries due to the predicted current path flows through a metal implant and/or the predicted current path flows through a part of the patient's body touching a grounded metal object. If so, the process sends a first warning message to a surgical staff and highlighting one or more locations of the potential tissue burn injuries on the one or more identified current paths among the first set of predicted current paths on a display.

In some embodiments, after sending the first warning message, the process further includes the steps of: receiving a new location of the return electrode of the monopolar electrosurgery tool on the patient's body; using the current-path-prediction model to generate a second set of predicted current paths inside the patient's body between the new location of the return electrode and the initial location of the active electrode; determining if any of the second set of predicted current paths can still cause potential tissue burn injuries due to the predicted current path flows through a metal implant and/or the predicted current path flows through a part of the patient's body touching a grounded metal object; and if so, sending a second warning message to the surgical staff and highlighting one or more locations of the potential tissue burn injuries on the one or more identified current paths among the second set of predicted current paths on the display.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1:
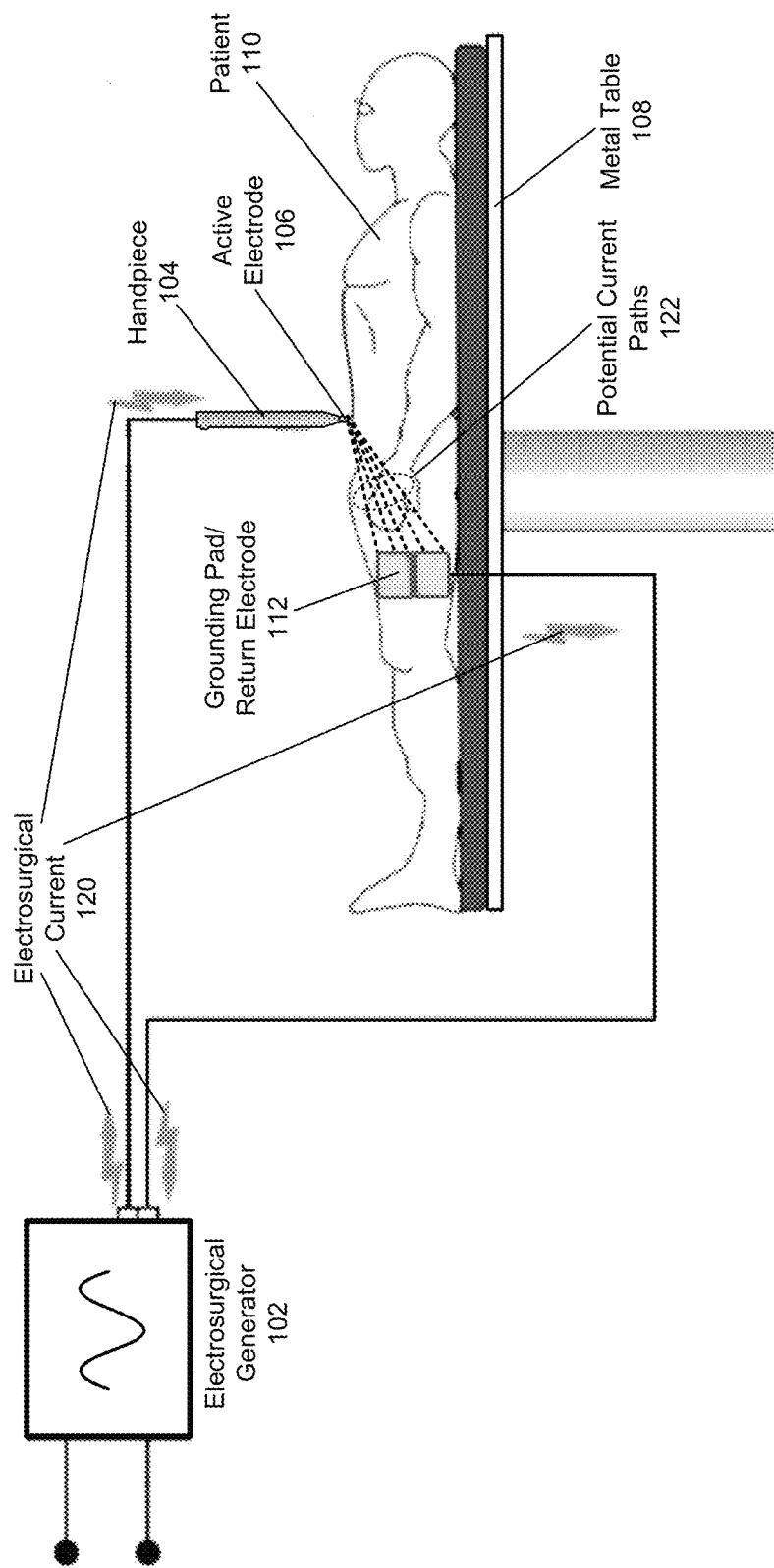
FIG. 1 illustrates an exemplary electrosurgery setup of using a monopolar electrosurgery tool on a patient in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

This patent disclosure provides various embodiments of predicting potential current paths from an active electrode of a monopolar electrosurgery tool to a return electrode/grounding pad (the terms "return electrode" and "grounding pad" are used interchangeably throughout this patent disclosure) of the monopolar electrosurgery tool based on analyzing electrical properties of tissues inside a patient's body, and evaluating and eliminating tissue burn risks associated with the predicted current paths. In some embodiments, a disclosed current-path-prediction technique is designed to predict a set of potential current paths from the active electrode to the grounding pad for any given geometrical configuration of the two electrodes on the patient's body. These predicted current paths can then be pictorially displayed on a three-dimensional (3D) scan of the patient's body or an endoscopic view of the patient's body and in relation to the display of any existing metal implant inside the patient's body, thereby allowing for visualizing points of tissue burn risks inside the patient's body. For example, when a predicted current path intersects the location of a metal implant inside the patient's body, a potential tissue burn risk is identified and the location where the current path meets the metal implant can be highlighted.

Based on the display of the predicted current paths and highlighted locations of tissue burn risks, surgical staff can choose to reposition the grounding pad of the monopolar electrosurgery tool to alter the potential current paths. The disclosed current-path-prediction technique can then be applied to the new electrodes configuration to generate another set of potential current paths from the active electrode to the new grounding pad location. Next, the potential tissue burn risks can be reevaluated for the new set of potential current paths inside the patient's body. If one or more tissue burn risks are identified for the new set of potential current paths, the grounding pad can be reposition again, and this current prediction-evaluation procedure can be repeated. Moreover, the predicted current paths can also reveal any accidental contact of a part of the patient body with a grounded metal object, such as the surgery table or a metal tray table. Such a body/metal contact can cause a current to bypass the grounding pad and flow to the body/metal contact location, causing accidental tissue burns. Hence, based on the evaluation outputs and display of the predicted current paths which highlights the locations of such burn risks, surgical staff can reposition the patient's body to prevent accidental contacts between the patient's body and the grounded metal objects.

FIG. 1 illustrates an exemplary electrosurgery setup 100 of using a monopolar electrosurgery tool on a patient 110 in accordance with some embodiments described herein. As shown in FIG. 1, the monopolar electrosurgery tool in electrosurgery setup 100 includes an electrosurgical generator 102, a handpiece 104, and an active electrode 106 which is attached to the end of handpiece 104. Electrosurgical generator 102 and handpiece 104 along with active electrode 106 at the tip of handpiece 104 is often referred to as an electrosurgery unit (ESU). Electrosurgical generator 102 is configured to generate electrical currents (e.g., electrical current 120) of various waveforms and deliver the currents to handpiece 104 and to the tip of active electrode 106. A surgeon can hold handpiece 104 to apply active electrode 106 to a surgical site on the abdomen of patient 110. As can be seen, when using the depicted monopolar electrosurgery tool in FIG. 1, active electrode 106 makes direct contact with the patient's tissue at the surgical site to effectuate a surgical effect with the electrical electrosurgical generator 102, such as cutting or cauterizing. Although FIG. 1 shows that the surgical site is on the abdomen of patient 110, a potential surgical site can be located at a different part of patient 110's body other than the patient's abdomen.

Also shown in FIG. 1, the depicted monopolar electrosurgery tool also includes a patient return electrode/grounding pad 112, which is placed somewhere else on the patient's body away from active electrode 106. For example, return electrode/grounding pad 112 is often placed on the opposite side of patient 110's body with respect to the surgical site (i.e., the location of active electrode 106). Note that grounding pad 112 is also connected to electrosurgical generator 102. Moreover, electrosurgical current 120, after being delivered to the surgical site by active electrode 106, will then flow through patient 110's body to grounding pad 112 which makes the patient's body a portion of the full current loop. Hence, electrosurgical current 120 generated by electrosurgical generator 102 flows from electrosurgical generator 102, to active electrode 106, through the patient's body to reach grounding pad 112, and returns to electrosurgical generator 102 from grounding pad 112 to complete the full current loop.

When electrosurgical current 120 flows through patient 110's body, heat can be generated along the current path inside the patient's body. In addition to forming part of the current loop, another important function of grounding pad 112 is to dissipate the heat generated inside the patient's body. A return electrode burn will occur if the heat produced, over time, is not safely dissipated by the size and/or the conductivity of grounding pad 112. Hence, grounding pad 112 is often designed with a significantly large size (e.g., no less than 2-inch×2-inch) and a sufficiently high conductivity. If the size and/or conductivity of grounding pad 112 are not properly configured, the heat generated inside the patient's body can accumulate at grounding pad 112, causing potential return-electrode burns.

To further reduce the risk of potential burns, in some embodiments, the location of grounding pad 112 should be chosen as close to the surgical site as possible. Such a grounding pad configuration can significantly reduce length of the current path within patient 110's body, which in turn reduces the risk of potential burns. Some other rules of placing grounding pad 112 which can help reduce the risk of potential burns include keeping grounding pad 112 clean, dry, well-vascularised, and over a large muscle mass. Moreover, grounding pad 112 should avoid bony prominences, adipose tissue, scar tissues, skins over implanted metal prostheses, hairy surfaces, and pressure points.

A person skilled in the art would appreciate that when electrosurgical current 120 flows through patient 110's body between active electrode 106 and grounding pad 112, the current tends to follow a path of least resistance. Hence, if patient 110 has one or more metal implants inside his/her body, electrosurgical current 120 may find a way to flow through one or more of these metal implants facilitated by the high conductivities of these metal implants. This scenario is clearly undesirable because electrosurgical current passing through a metal implant can not only damage a functional metal implant, such as a cardiac pacemaker, but cause tissue/organ burn injuries if the metal implant becomes heated up over time. Moreover, if the metal implant is a cardiac pacemaker, electrosurgical current 120 can be led through the heart, causing serious risks of cardiac shock.

Hence, during an electrosurgery procedure, potential burns and injuries can occur if the following scenarios are not analyzed prior to applying electrosurgery current to the patient.

Metal implants: if patient 110 has one or more metal implants inside his/her body, such as a cardiac pacemaker or a metal orthopedic implant, such metal implants need to be determined a-priori. If the existing metal implants are not properly determined, the aforementioned electrical burn injuries can occur if one or more of the metal implants become part of the current pathway. For example, if grounding pad 112 in FIG. 1 happens to be placed on patient 110's skin directly over a metal implant of patient 110, electrosurgical current 120 is highly-likely to flow through this metal implant.

Patient touching a grounded metal object: metal operating table 108 in FIG. 1 where patient 110 lies is usually grounded. Hence, if any part of patient 110's body, such as a hand or an arm accidentally touches metal table 108, electrosurgical current 120 can directly flow from active electrode 106 to the location where patient 110's body touches metal table 108, while completely bypassing grounding pad 112 (e.g., in a configuration where grounding pad 112 is placed at a location further away from active electrode 106 than the location where patient 110's body is in contact with metal table 108). Hence, it is necessary to position and insulate patient 110 so that she or he is not touching any grounded metal object.

Note that for a patient with one or more metal implants, if such a patient accidentally touches a grounded metal object during an electrosurgical process, the risk of electrical burn injuries faced by such a patient becomes significantly higher than another patient without any metal implant.

Note that for each unique patient 110, if the potential current paths from active electrode 106 to grounding pad 112 can be predicted prior to performing the electrosurgery on the patient, then each of the predicted current paths can be evaluated to determine if any potential current path has potential risks of causing burn injuries or other electrical damages to the tissues along the given current path. In particular, one or more of the potential current paths associated with high probabilities can be evaluated with high priorities because they are the more likely paths that the current can take. Based on this evaluation, surgical staff can be alerted for any given potential path determined to have electrical burn risks, e.g., if a given potential current path is determined to flow through a metal implant inside patient 110's body. As a result, the informed surgical staff can make changes to the electrosurgery configuration for patient 110, e.g., by repositioning grounding pad 112 on patient 110's body or by repositioning patient 110 on operation table 108. The change to the electrosurgery setup 100 would result in the potential current paths to be altered. Next, the potential current paths from active electrode 106 to grounding pad 112 can be re-determined and re-evaluated prior to performing the electrosurgery procedure on patient 110. Through this recursive procedure of predicting (the potential current paths)/evaluating (tissue burn risks)/adjusting (the grounding pad and/or the patient), potential burn and other electrical injuries during the electrosurgery procedure can be strategically avoided.

While it is generally assumed that a current will follow the path of the least resistance from a point A to a point B, the current will actually take multiple paths to flow from point A to point B. Hence, electrosurgery current 120 can also take multiple potential paths 122 (illustrated as the set of dash lines between active electrode 106 and grounding pad 112) to flow from active electrode 106 to grounding pad 112. Because an electrosurgery tool uses high frequency current, the impedance/dielectric properties of various tissues within patient 110's body play significant roles in determining the current pathways. It has been found that the dielectric property of a tissue in the human body can be a direct function of the water content in the tissue. In other words, if the water content within a given tissue can be determined, then the dielectric property of the tissue can be uniquely determined. Once the dielectric properties of the various tissues within patient 110's body are determined, it becomes possible to predict the one or more paths of least resistance from active electrode 106 to grounding pad 112. In some embodiments, for each of the multiple predicted current paths 122, a probability value is also determined for the given current path, e.g., which can be partially based on the overall resistance of the given current path. More details of determining the probability for each predicted current path are provided below such as in conjunction with FIG. 2.

It can be reasonably assumed that the water contents of various tissues are not very different from one patient to another. Hence, in some embodiments, an average value of the water content for a given type of tissue can be determined from different samples of the given type of tissue and used as a common value of the water content for all patients. In other embodiments, patients can be categorized based on a certain criterion, such as the age group, and as a result slightly different water content values for the same type of tissue can be determined for patients belong to different categories of the criterion, such as different age groups. Note that age group is just one of the possible criteria to categorize patients into categories and assign slightly different values of water content to different categories. Other possible criteria which can be used to categorize patients can include gender, race/ethnicity, and body mass index (BMI), among others.

Hence, in some embodiments, prior to predicting potential current paths 122 of electrosurgery current 120 in patient 110's body, a look-up table containing estimated water contents of various types of tissues in the human body can be constructed. For example, some of these water content values are already available from scientific studies. Moreover, because the dielectric constant is a direct function of the water content, instead of constructing the look-up table for the estimated water contents, some embodiments can construct a look-up table containing estimated dielectric constants of various types of tissues in the human body.

In some embodiments, prior to predicting the potential current paths 122, the tissues in patient 110's body along the way from active electrode 106 to grounding pad 112 need to be identified. In some embodiments, to identify these tissues, an endoscope can be used to capture video images of the anatomical structures inside the patient's body, and a segmentation technique can be applied to the captured anatomical structures to identify various tissues between active electrode 106 and grounding pad 112.

In many scenarios, a complete tissue structure between the active electrode and the grounding pad can not be fully determined solely based on the endoscope view due to the limited field of view of the endoscope camera comparing to the actual region of interest. Hence, in some embodiments, a three-dimensional (3D) scan of patient 110's body can be performed to determine the necessary anatomy of the patient's body, including the organs and tissues between active electrode 106 and grounding pad 112, as well as the existence of one or more metal implants (e.g., a cardiac pacemaker) inside the patient's body. Note that based on the 3D scan, the dimensions of the tissues (e.g., the thicknesses of the tissues in the vertical direction and the lengths and widths of the tissues in the horizontal directions) between active electrode 106 and grounding pad 112 and the dimensions of the metal implants (if any) can be determined. In some embodiments, when the option of performing a 3D scan of the patient's body is not available, a standard human anatomy model can be used to supplement the endoscope video data so that a complete tissue structure between the active electrode and the grounding pad can be constructed. However, in these embodiments, the metal implant information can not be supplemented by the standard human anatomy model and therefore has to be acquired a-priori, e.g., through an inquiry of patient's medical history, and then manually entered into a model of the patient's body.

Note that sometimes the color of a given tissue can be used as an indicator of the water content within the tissue. For example, a darker colored tissue is often an indicator of lower water content in the tissue than another tissue with brighter color. Hence, the color information from the segmented endoscope video images of a given tissue can be used to augment the water content or dielectric constant information (i.e., an average value) already available for the given type of tissue. More specifically, let's assume that a look-up table is available with the average values of the tissues of a human body. The color information later obtained for a given tissue, e.g., from an endoscope video can be converted into a delta value/modifier to either increase or decrease the corresponding average value of the given tissue stored in the look-up table. In some embodiments, the color information of a tissue can be automatically extracted from the endoscope video images and then automatically processed to determine the amount of adjustment to the average value of the tissue.

Based on the above-described information, i.e., (1) the look-up table for the dielectric constants and/or water contents; (2) the segmented 3D anatomical structures of the patient's body identifying various tissues between the active electrode and the grounding pad; and (3) supplementary color information of the identified tissues, potential current paths 122 from active electrode 106 to grounding pad 112 can be predicted. More specifically, a current path model can be constructed, which receives some or all of the following inputs: (1) the locations of active electrode 106 and grounding pad 112; (2) the segmented 3D anatomical scan of patient 110's body identifying various tissues between active electrode 106 and grounding pad 112; and (3) endoscope view inside patient 110's body showing supplementary color information of some or all of the identified tissues. The current path model can also receive the metal implant information (if any) which can be obtained either based on the 3D anatomical scan or through an inquiry of patient's medical history. Based on the segmented 3D anatomical scan and the look-up table containing estimated dielectric constants of various types of tissues in human body, the current path model can construct a 3D resistance map between active electrode 106 and grounding pad 112 and subsequently predict multiple potential current paths 122 (of least resistance) from active electrode 106 to grounding pad 112.

One reason that the disclosed current path model can generate multiple potential current paths is that, current does not always follow the path of least resistance but can take other paths with a probability in reverse proportion to the resistances of the paths. For each predicted current path by the current path model, an overall resistance between the active electrode and the grounding pad can be estimated based on the identified tissues and the associated dielectric constants along the current path. The estimated resistance along each predicted current path can be used to generate a probability for the given current path, i.e., a lower resistance current path can be assigned with a higher probability value, whereas a high resistance current path can be assigned a lower probability value. For example, if among the multiple potential current paths, there is one current path with the overall lowest resistance, this current path would likely to get the highest probability among the multiple potential current paths. In some embodiments, multiple potential current paths can be identified as a set of current paths associated with the top N (e.g., N=5) lowest resistances.

Another reason that the generated potential current paths 122 can have different associated probabilities is that some of the input values to the disclosed current path model are statistical values, i.e., instead of being a single value, are of a range of values. For example, each of the estimated dielectric constants in the look-up table of the tissues can be expressed in terms of a mean value and a confidence interval of a range of values around the mean value. As another example, each extracted physical dimension, such as the vertical distance or the horizontal distance between active electrode 106 and grounding pad 112 can have an uncertainty associated with the measurement. As a result, the current path model can generate multiple predicted current paths 122 with different probabilities by taking into account these statistical values, variations, and uncertainties in the calculations.

In some embodiments, after generating multiple predicted current paths, a subset of the predicted current paths having the highest probabilities can be displayed pictorially on the screen. For example, these predicted current paths can be displayed illustratively on a 3D "see-through" view depicting the patient's body, wherein the 3D view can be based on a 3D scan of the patient's body. More specifically, the 3D view of the patient's body can show the locations of the surgical site/active electrode 106 and grounding pad 112 as well as the locations and dimensions of one or more metal implants inside the patient's body if there is any. The predicted current paths 122 can be illustrated in the 3D view as lines connecting active electrode 106 and grounding pad 112, as illustrated in FIG. 1. In some embodiments, the probability value associated with each displayed current path can be shown on that current path. As such, surgical staff can receive a complete picture of each illustrated current path, e.g., by observing the illustrated current path from different viewing angles by rotating the 3D view of the patient body. In some embodiments, the predicted current paths can be used to augment the endoscope video which shows 3D images of the anatomical structures around the surgical site.

In addition to pictorially displaying some of the predicted current paths, the locations of potential tissue burn injures due to currents flowing through metal implants and/or body parts in contact with grounded metal objects can be highlighted on the display to aid the surgical staff in determining the at-risk locations. In some embodiments, the entire current path which includes one or more at-risk locations can be highlighted. Based on the displayed and highlighted current paths, it becomes obvious to the surgical staff if any of the high probability current paths is passing through a metal implant within the patient's body or bypassing grounding pad 112 through a grounded metal object that the patient is accidentally touching.

Once the surgical staff is informed of the predicted current paths and potential burn risks associated with the current paths, the surgical staff can then make an informed decision on whether grounding pad 112 needs to be moved to a different location, or whether the patient's position needs to be adjusted. Note that after the surgical staff has made changes to grounding pad 112, the current path model can be applied to the new/modified electrosurgery setup to predict another set of potential current paths based on the new grounding pad placement. Hence, the above-described process of predicting current paths and risks, and making changes to the electrosurgery setup 100 can be repeated. However, if after a number of iterations, the burn risks associated with metal implants can not be eliminated with grounding pad adjustments, the surgical staff may decide whether using monopolar electrosurgery tool itself should be avoided in the given procedure and alternative electrosurgical tools should be explored in place of the monopolar electrosurgery tool.

Figure 2:
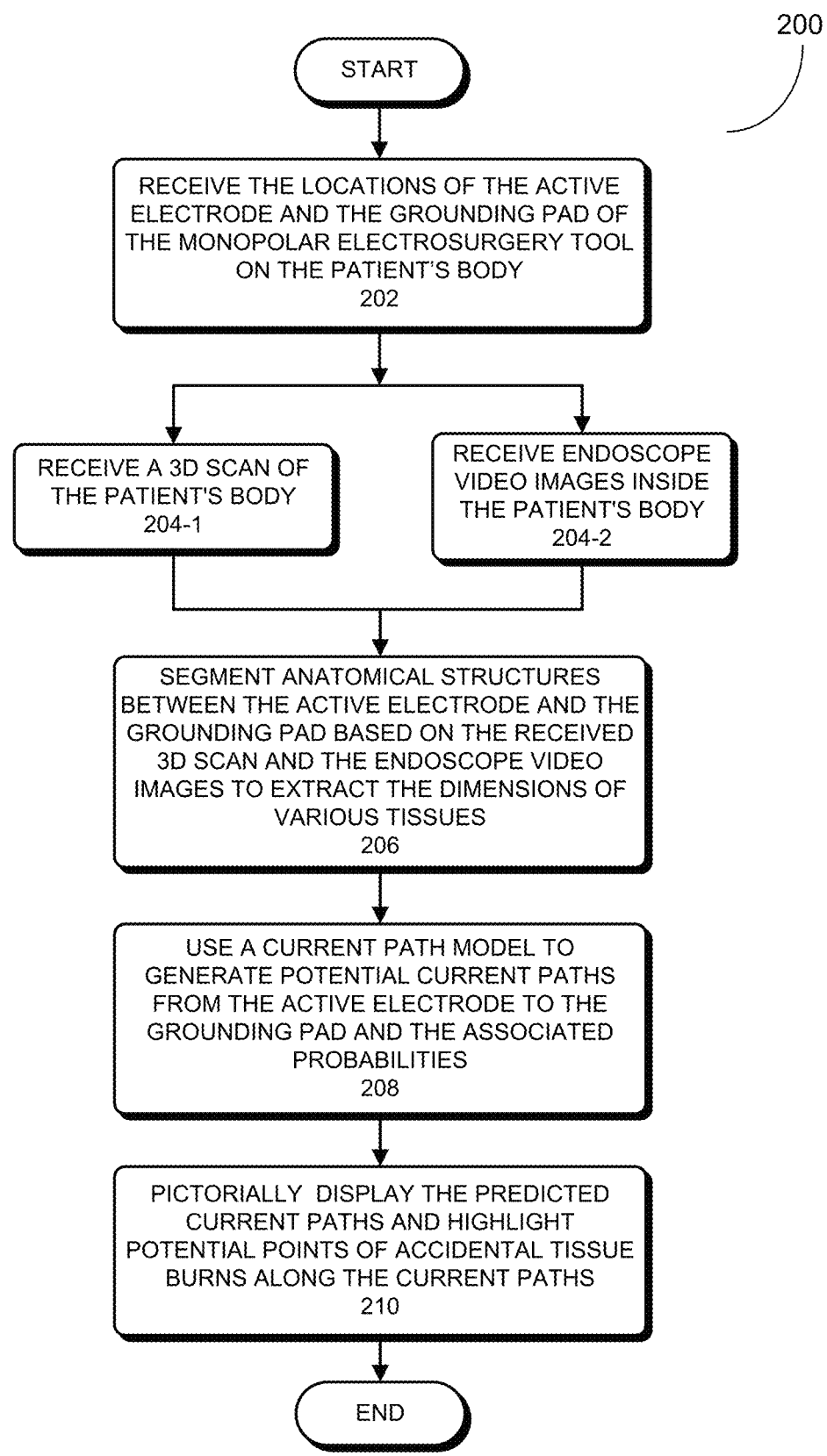
FIG. 2 presents a flowchart illustrating an exemplary process for predicting potential current paths within a patient's body when using a monopolar electrosurgery tool during an electrosurgery in accordance with some embodiments described herein.

FIG. 2 presents a flowchart illustrating an exemplary process 200 for predicting potential current paths within a patient's body when using a monopolar electrosurgery tool during an electrosurgery in accordance with some embodiments described herein. In one or more embodiments, one or more of the steps in FIG. 2 may be omitted, repeated, and/or performed in a different order. Accordingly, the specific arrangement of steps shown in FIG. 2 should not be construed as limiting the scope of the technique.

As can be seen in FIG. 2, process 200 begins by receiving the locations of the active electrode of the monopolar electrosurgery tool and the grounding pad of the monopolar electrosurgery tool on the patient's body (step 202). Process 200 also receives a 3D scan of the patient's body (step 204-1). For example, the 3D scan of the patient can be a CT scan or an X-ray scan. In some embodiments, the 3D scan can be limited to a part of the patient's body between the location of the active electrode and the location of the grounding pad because this is the region that most likely contains the potential current paths. As shown in FIG. 2, process 200 also receives endoscope video images which capture the anatomical structures inside the patient's body along the way between the active electrode and the grounding pad (step 204-2). Next, process 200 segments anatomical structures between the locations of the active electrode and the grounding pad based on the received 3D scan and the endoscope video images to extract the sizes/dimensions of various tissues between the active electrode and the grounding pad (step 206). In some embodiments, if the 3D scan is available, the process can also extract from the 3D scan, the locations and dimensions of one or more metal implants inside the patient's body.

Note that in some embodiments, 3D scan of the patient body is not available prior to the electrosurgery procedure (i.e., without step 204-1). In such embodiments, step 206 only uses the endoscope video images from step 204-2 to extract the sizes/dimensions of various tissues between the active electrode and the grounding pad. In some other embodiments, endoscope video images inside the patient's body between the active electrode and the grounding pad are not available or only partially available (i.e., to only cover a portion of the distance between the active electrode and the grounding pad). This can be due to difficulties to access the full distance between the active electrode and the grounding pad or to place the endoscopic camera near the surgical site. In such embodiments, step 206 only uses the 3D scan data from step 204-1 or the 3D scan data in combination with the partial endoscope data to extract the sizes/dimensions of various tissues between the active electrode and the grounding pad.

As described above, prior to performing process 200, a look-up table containing estimated dielectric constants of various types of tissues in the human body has been constructed. Hence, the extracted anatomical structures of the tissues based on the 3D scan and endoscopy video images can be augmented with the corresponding estimated dielectric constants. In some embodiments, the color information from the endoscope video images of the identified tissues can be used to modify the average dielectric-constant values of the corresponding tissues available from the look-up table. To do so, the color information of each identified tissue can be automatically extracted from the endoscope video images and then automatically processed to determine an amount of adjustment to the average dielectric-constant value of the identified tissue. For example, a significantly brighter color of a given identified tissue than an average color of the given tissue usually suggests higher water content in the tissue which would require a positive adjustment to increase the average dielectric-constant value for the given identified tissue. In contrast, a significantly darker color of a given identified tissue than an average color of the given tissue usually suggests lower water content in the tissue which would require a negative adjustment to decrease the average dielectric constant value for the given identified tissue.

Next, process 200 uses a current path model and (1) the extracted dimensions of the various tissues augmented with the estimated dielectric constants; and (2) the locations of the active electrode and the grounding pad as inputs to the current path model to generate multiple potential current paths from the active electrode and the grounding pad and the probabilities associated with the potential current paths (step 208). For example, process 200 can use an electrical current model constructed for human body which computes current paths inside the human body based on the concept of path of least resistance. Note that each generated potential current path can have a probability value as a result of multiple factors. For example, the associated probability value can be a result of uncertainties in the input values to the current path model. For example, each of the estimated dielectric constants in the look-up table of the tissues can be expressed in terms of a mean value and a confidence interval of a range of values around the mean value. As another example, each extracted physical dimension, such as the vertical distance or the horizontal distance between active electrode 106 and grounding pad 112 can have an uncertainty associated with the corresponding measurement.

Another factor which can affect the probability value of a generated current path is that current does not always follow the path of least resistance but can take other paths with a probability in reverse proportion to the resistances of the paths. In some embodiments, multiple potential current paths can be identified as a set of current paths associated with the lowest resistances, and each of the multiple current paths can be assigned a probability value in reverse proportion to the resistance of that current path. For example, if among the multiple potential current paths, there is one current path with the overall lowest resistance, this current path would likely to get the highest probability among the multiple potential current paths. However, if there are two lowest-resistance current paths both having a near-identical overall lowest resistance, these two potential current paths would likely to get very similar probabilities.

After generating the potential current paths, process 200 can pictorially display the predicted current paths on a monitor, e.g., on a 3D view of the patient's body which can also display the locations and dimensions of one or more metal implants inside the patient's body if there is any. In some embodiments, the predicted current paths can also be displayed on the endoscope video. If a surgeon is using a head-mounted display to view to the endoscope video, the predicted current paths can also be presented in the view in a manner of augmented reality. Whether the predicted current paths are displayed in conjunction with the 3D view of the patient's body or the endoscope view of the patient's body, the displayed current paths can also identify/highlight potential locations of accidental tissue burns due to metal implants and/or body/metal objects contacts (step 210). In some embodiments, instead of displaying all of the generated potential current paths in the 3D view or the endoscope view of the patient's body, only the few of the predicted current paths associated with the highest probabilities are displayed (e.g., the top 3-5 current paths).

Figure 3:
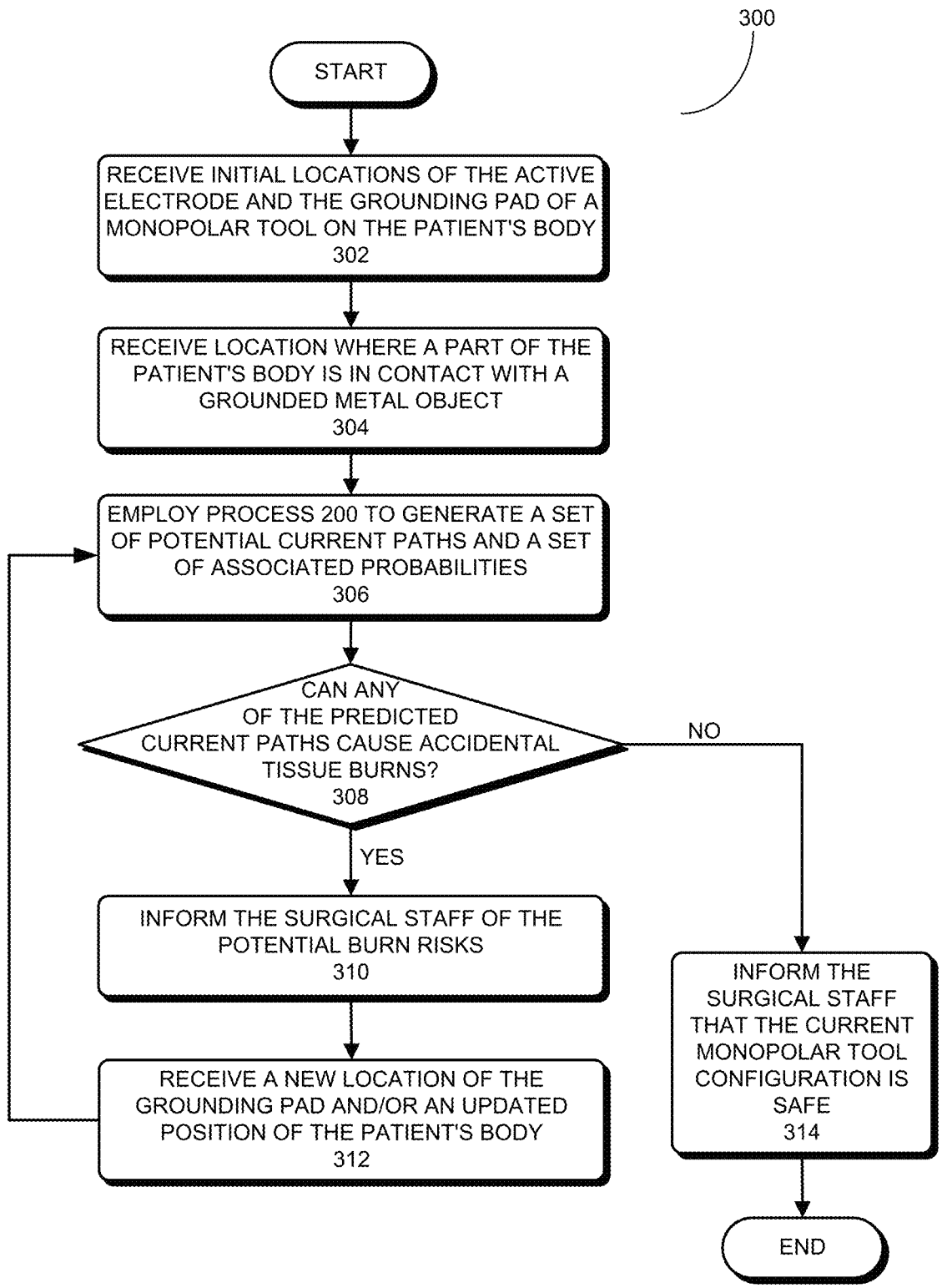
FIG. 3 presents a flowchart illustrating an exemplary process for using a potential-current-path prediction procedure to eliminate the risks of accidental tissue burns when using a monopolar electrosurgery tool for electrosurgery in accordance with some embodiments described herein.

FIG. 3 presents a flowchart illustrating an exemplary process for using a potential-current-path prediction procedure to eliminate the risks of accidental tissue burns when using a monopolar electrosurgery tool for electrosurgery in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Processing 300 may begin by receiving initial locations of the active electrode and the grounding pad of a monopolar tool on the patient's body (step 302). Processing 300 can also receive a location of a part of the patient's body is in contact with a grounded metal object (step 304). Next, process 300 can employ process 200 described above to generate a set of potential current paths between the initial locations of the active electrode and the grounding pad and a set of associated probabilities (step 306). The outputs from step 306 can be presented to the surgical staff pictorially on a display as described above. Based on the predicted current paths, process 300 next determines if any of the predicted current paths can cause accidental tissue burns due to current flowing through metal implants and/or a part of the body in contact with a metal object (step 308). In some embodiments, when analyzing the electrical burn risks, process 300 determines if any of the top few current paths of the highest probabilities (e.g., the top 3-5 highest-probability current paths) flows through a metal implant and/or to the location where a body/metal object contact.

If electrical burn risks are identified at step 308, process 300 informs the surgical staff of the potential burn risks, e.g., by sending a warning message/alert and/or highlighting the locations of the potential burn risks on the one or more identified high-risk current paths on a display (step 310). Based on the warning/alert messages from step 310, surgical staff can make an informed decision on whether to reposition the grounding pad and/or whether the patient's position needs to be changed in an effort to eliminate or significantly reduce the predicted electrical burn risks. Hence, process 300 next receives a new location of the grounding pad of the monopolar tool on the patient's body and/or updated information regarding any part of the patient's body is in contact with the grounded metal object (step 312). Next, process 300 returns to step 306 to generate an updated set of potential current paths and a set of associated probabilities and subsequently reevaluate the electrical burn risks for the updated set of potential current paths (step 308).

Hence, steps 306-312 can be repeated as a loop if electrical burn risks are repeated identified at step 308. Returning to step 308, if process 300 determines that the currently predicted current paths do not have electrical burn risks, process 300 can send a message to the surgical staff to inform that the current monopolar tool configuration is safe and optionally display a few predicted current paths with the highest probabilities on the display (step 314). Subsequently, the electrosurgery procedure can proceed without potential electrical burn risks. However, in some embodiments, if the adjustment/reevaluation loop of steps 306-312 has been repeated for a predetermined number of times but step 308 continues to identify electrical burn risks, the surgical staff may conclude that using the monopolar tool should be avoided for the given electrosurgery procedure and alternative tools should be considered.

Figure 4:
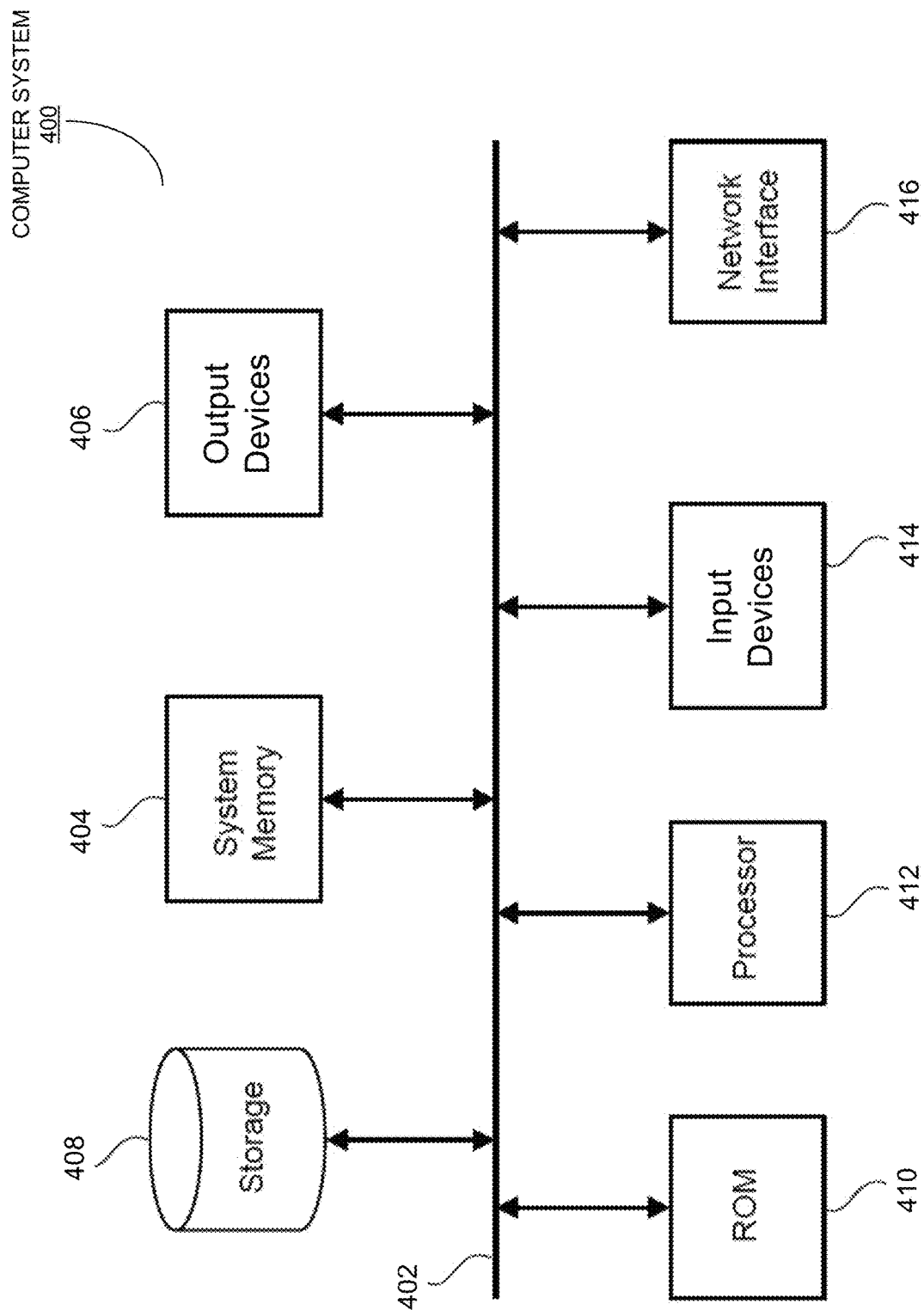
FIG. 4 conceptually illustrates a computer system with which some embodiments of the subject technology can be implemented.

FIG. 4 conceptually illustrates a computer system with which some embodiments of the subject technology can be implemented. Computer system 400 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 400 includes a bus 402, processing unit(s) 412, a system memory 404, a read-only memory (ROM) 410, a permanent storage device 408, an input device interface 414, an output device interface 406, and a network interface 416. In some embodiments, computer system 400 is a part of a robotic surgical system.

Bus 402 collectively represents all system, peripheral, and chipset buses that communicatively connect the numerous internal devices of computer system 400. For instance, bus 402 communicatively connects processing unit(s) 412 with ROM 410, system memory 404, and permanent storage device 408.

From these various memory units, processing unit(s) 412 retrieves instructions to execute and data to process in order to execute various processes described in this patent disclosure, including the above-described processes of predicting potential current paths when using a monopolar electrosurgical tool and using a potential-current-path prediction procedure to eliminate the risk of accidental tissue burns when using a monopolar electrosurgery tool in conjunction with FIGS. 2 and 3. The processing unit(s) 412 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 412 can be a single processor or a multi-core processor in different implementations.

ROM 410 stores static data and instructions that are needed by processing unit(s) 412 and other modules of the computer system. Permanent storage device 408, on the other hand, is a read-and-write memory device. This device is a non-volatile memory unit that stores instructions and data even when computer system 400 is off. Some implementations of the subject disclosure use a mass-storage device (such as a magnetic or optical disk and its corresponding disk drive) as permanent storage device 408.

Other implementations use a removable storage device (such as a floppy disk, flash drive, and its corresponding disk drive) as permanent storage device 408. Like permanent storage device 408, system memory 404 is a read-and-write memory device. However, unlike storage device 408, system memory 404 is a volatile read-and-write memory, such as a random access memory. System memory 404 stores some of the instructions and data that the processor needs at runtime. In some implementations, various processes described in this patent disclosure, including the above-described processes of predicting potential current paths when using a monopolar electrosurgical tool and using a potential-current-path prediction procedure to eliminate the risk of accidental tissue burns when using a monopolar electrosurgery tool in conjunction with FIGS. 2 and 3, are stored in system memory 404, permanent storage device 408, and/or ROM 410. From these various memory units, processing unit(s) 412 retrieve instructions to execute and data to process in order to execute the processes of some implementations.

Bus 402 also connects to input and output devices 414 and 406. Input devices 414 enable the user to communicate information to and select commands for the computer system. Input devices 414 can include, for example, alphanumeric keyboards and pointing devices (also called "cursor control devices"). Output devices 406 enable, for example, the display of images generated by computer system 400. Output devices 406 can include, for example, printers and display devices, such as cathode ray tubes (CRT) or liquid crystal displays (LCD). Some implementations include devices such as a touchscreen that functions as both input and output devices.

Finally, as shown in FIG. 4, bus 402 also couples computer system 400 to a network (not shown) through a network interface 416. In this manner, the computer can be a part of a network of computers (such as a local area network ("LAN"), a wide area network ("WAN"), an intranet, or a network of networks, such as the Internet. Any or all components of computer system 400 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for predicting potential current paths within a patient's body when using a monopolar electrosurgery tool on the patient, the method comprising:
  receiving locations of one active electrode and a return electrode of the monopolar electrosurgery tool on the patient's body;
  identifying a set of tissues between the locations of the one active electrode and the return electrode;
  augmenting each of the set of identified tissues with a corresponding value of an electrical property;
  using a current path model, the set of identified tissues, and the set of corresponding values of the electrical property to predict a plurality of current paths between the one active electrode and the return electrode; and
  displaying at least one predicted current path in the plurality of predicted current paths to facilitate identifying at-risk locations along the predicted current paths.

2. The computer-implemented method of claim 1, wherein identifying the set of tissues between the locations of the one active electrode and the return electrode includes:
  receiving a three-dimensional (3D) scan of the patient's body;
  segmenting anatomical structures between the locations of the one active electrode and the return electrode based on the received 3D scan; and
  identifying the set of tissues from the segmented anatomical structures.

3. The computer-implemented method of claim 2, wherein identifying the set of tissues between the locations of the one active electrode and the return electrode includes:
  receiving an endoscope video which captures anatomical structures inside the patient's body along the way between the one active electrode and the return electrode; and
  segmenting the captured anatomical structures to identify the set of tissues.

4. The computer-implemented method of claim 2, wherein identifying the set of tissues from the segmented anatomical structures further includes identifying a set of dimensions for each of the set of identified tissues.

5. The computer-implemented method of claim 2, wherein the method further comprises:
  extracting from the 3D scan, locations and dimensions of one or more metal implants inside the patient's body; and
  providing the extracted locations and dimensions of the one or more metal implants to the current path model as inputs for predicting the plurality of current paths.

6. The computer-implemented method of claim 1, wherein the electrical property is a dielectric property, and wherein augmenting each of the set of identified tissues with a corresponding value of the electrical property includes using a look-up table containing estimated dielectric constants of various types of tissues within a human body.

7. The computer-implemented method of claim 6, wherein augmenting each of the set of identified tissues with a corresponding value of the electrical property further includes:
  extracting color information for an identified tissue in the set of identified tissues from endoscope video images of anatomical structures inside the patient's body along the way between the one active electrode and the return electrode;
  converting the color information into a modifier to modify a corresponding dielectric constant value associated with the identified tissues from the look-up table; and
  augmenting the identified tissue with the modified dielectric constant value.

8. The computer-implemented method of claim 1, wherein predicting the plurality of current paths from the one active electrode to the return electrode further includes computing a probability value for each of the plurality of predicted current paths, wherein a predicted current path in the plurality of predicted current paths having a lower overall resistance is associated with a higher probability value.

9. The computer-implemented method of claim 8, wherein the method further comprises:
  displaying one or more predicted current paths in the plurality of predicted current paths which has the highest probability values; and
  for each of the displayed predicted potential current paths, highlighting one or more locations of potential tissue burn injuries due to the predicted current path flows through a metal implant and/or the predicted current path flows through a part of the patient's body touching a grounded metal object.

10. A system for predicting potential current paths within a patient's body when using a monopolar electrosurgery tool on the patient, comprising:
  one or more processors;
  a memory coupled to the one or more processors; and
  wherein the one or more processors are configured to:
    receive locations of one active electrode and a return electrode of the monopolar electrosurgery tool on the patient's body;
    identify a set of tissues between the locations of the one active electrode and the return electrode;
    augment each of the set of identified tissues with a corresponding value of an electrical property;
    use a current path model, the set of identified tissues, and the set of corresponding values of the electrical property to predict a plurality of current paths between the one active electrode and the return electrode; and
    display at least one predicted current path in the plurality of predicted current paths to facilitate identifying at-risk locations along the predicted current paths.

11. The system of claim 10, wherein the system identifies the set of tissues between the locations of the one active electrode and the return electrode by:
  receiving a three-dimensional (3D) scan of the patient's body;
  segmenting anatomical structures between the locations of the one active electrode and the return electrode based on the received 3D scan; and
  identifying the set of tissues from the segmented anatomical structures.

12. The system of claim 11, wherein the system identifies the set of tissues between the locations of the one active electrode and the return electrode by:
   receiving an endoscope video which captures anatomical structures inside the patient's body along the way between the one active electrode and the return electrode; and
   segmenting the captured anatomical structures to identify the set of tissues.

13. The system of claim 11, wherein identifying the set of tissues from the segmented anatomical structures further includes identifying a set of dimensions for each of the set of identified tissues.

14. The system of claim 11, wherein the one or more processors are further configured to:
   extract from the 3D scan, locations and dimensions of one or more metal implants inside the patient's body; and
   provide the extracted locations and dimensions of the one or more metal implants to the current path model as inputs for predicting the plurality of current paths.

15. The system of claim 10, wherein the electrical property is a dielectric property, and wherein augmenting each of the set of identified tissues with a corresponding value of the electrical property includes using a look-up table containing estimated dielectric constants of various types of tissues within a human body.

16. The system of claim 10, wherein augmenting each of the set of identified tissues with a corresponding value of the electrical property further includes:
   extracting color information for an identified tissue in the set of identified tissues from endoscope video images of anatomical structures inside the patient's body along the way between the one active electrode and the return electrode;
   converting the color information into a modifier to modify a corresponding dielectric constant value associated with the identified tissues from the look-up table; and
   augmenting the identified tissue with the modified dielectric constant value.

17. The system of claim 10, wherein predicting the plurality of current paths from the one active electrode to the return electrode further includes computing a probability value for each of the plurality of predicted current paths, wherein a potential predicted current path in the plurality of predicted current paths having a lower overall resistance is associated with a higher probability value.

18. The system of claim 17, wherein the system further includes a display device, and wherein the one or more processors are further configured to:
   display on the display device one or more predicted current paths in the plurality of predicted current paths which has the highest probability values; and
   for each of the displayed predicted current paths, highlight one or more locations of potential tissue burn injuries due to the predicted current path flows through a metal implant and/or the predicted current path flows through a part of the patient's body touching a grounded metal object.

19. A computer-implemented method for using a current-path-prediction procedure to eliminate risks of accidental tissue burns when using a monopolar electrosurgery tool on a patient, the method comprising:
   receiving initial locations of one active electrode and a return electrode of the monopolar electrosurgery tool on the patient's body;
   using a current-path-prediction model to generate a first set of two or more predicted current paths inside the patient's body between the initial locations of the one active electrode and the return electrode;
   determining if any of the first set of two or more predicted current paths can cause potential tissue burn injuries due to the predicted current path flows through a metal implant and/or the predicted current path flows through a part of the patient's body touching a grounded metal object; and
   if so, sending a first warning message to a surgical staff and highlighting one or more locations of the potential tissue burn injuries on the one or more identified current paths among the first set of two or more predicted current paths on a display.

20. The computer-implemented method of 19, wherein after sending the first warning message, the method further comprises:
   receiving a new location of the return electrode of the monopolar electrosurgery tool on the patient's body;
   using the current-path-prediction model to generate a second set of two or more predicted current paths inside the patient's body between the new location of the return electrode and the initial location of the one active electrode;
   determining if any of the second set of two or more predicted current paths can still cause potential tissue burn injuries due to the predicted current path flows through a metal implant and/or the predicted current path flows through a part of the patient's body touching a grounded metal object; and
   if so, sending a second warning message to the surgical staff and highlighting one or more locations of the potential tissue burn injuries on the one or more identified current paths among the second set of two or more predicted current paths on the display.

* * * * *